United States Patent
McDonald et al.

(10) Patent No.: US 7,214,391 B2
(45) Date of Patent: May 8, 2007

(54) BOTANICAL EXTRACT COMPOSITIONS AND PROCESS FOR PREPARING SAME

(75) Inventors: John H. McDonald, Murray, UT (US); Sean C. McDonald, Midvale, UT (US); Larry D. Lundmark, Maple Grove, MN (US); Jon J. Kabara, Galena, IL (US); John A. Garruto, Encinitas, CA (US)

(73) Assignee: USANA Health Sciences, Inc., Salt Lake City, UT (US)

( * ) Notice: Subject to any disclaimer, the term of this patent is extended or adjusted under 35 U.S.C. 154(b) by 410 days.

(21) Appl. No.: 10/610,518

(22) Filed: Jun. 30, 2003

(65) Prior Publication Data

US 2004/0265263 A1    Dec. 30, 2004

(51) Int. Cl.
*A01N 65/00* (2006.01)

(52) U.S. Cl. ...................................... 424/729

(58) Field of Classification Search ............. None
See application file for complete search history.

(56) References Cited

U.S. PATENT DOCUMENTS

| | | | |
|---|---|---|---|
| 3,772,446 A | 11/1973 | Larrson |
| 3,934,029 A | 1/1976 | Kabara |
| 3,934,030 A | 1/1976 | Kabara |
| 3,934,031 A | 1/1976 | Kabara |
| 3,934,035 A | 1/1976 | Kabara |
| 4,002,775 A | 1/1977 | Kabara |
| 4,067,997 A | 1/1978 | Kabara |
| 4,189,481 A | 2/1980 | Kabara |
| 4,217,364 A | 8/1980 | Kabara |
| 4,557,935 A | 12/1985 | af Ekenstam et al. |
| 5,208,257 A | 5/1993 | Kabara |
| 5,736,574 A | 4/1998 | Burnier et al. |
| 5,744,062 A | 4/1998 | Dahms et al. |
| 5,922,313 A | 7/1999 | Steward et al. |
| 5,925,364 A | 7/1999 | Ribier et al. |
| 5,948,416 A | 9/1999 | Wagner et al. |
| 6,066,328 A | 5/2000 | Ribier et al. |
| 6,146,660 A | 11/2000 | Terren et al. |
| 6,211,238 B1 | 4/2001 | Castillo et al. |
| 6,214,327 B1 | 4/2001 | Steward et al. |
| 6,274,124 B1 | 8/2001 | Vollhardt |
| 6,281,203 B1 | 8/2001 | Touzan et al. |
| 6,296,859 B1 | 10/2001 | Stoltz |
| 6,495,498 B2 | 12/2002 | Niemiec et al. |
| 6,521,241 B1 | 2/2003 | Minerath, III et al. |
| 6,524,594 B1 | 2/2003 | Santora et al. |
| 6,638,978 B1 | 10/2003 | Kabara |

FOREIGN PATENT DOCUMENTS

EP        001175896 A1 *  2/2001

OTHER PUBLICATIONS

Haque et al., Antimicrobial Agents & Chemotherapy (1974), 5: 447-452. Effect of ethylenediaminetetraacetic acid and related chelating agents on whole cells on gram-negative bacteria.*
G. Dahms, "Properties of O/W Emulsions with Anisotropic Lamellar Phases," Cosmetics & Toiletries 101:113-115, (1986).
G. M. Eccleston, "Multiple-Phase Oil-in-Water Emulsions", J. Soc. Cosmet. Chem. 41:1-22 (Jan./Feb. 1990).
Chapter 3 "Water Activity and Self-Preserving Formulas" (Preservative-Free and Self-Preserving Cosmetics and Drugs Principles and Practice, Kabara and Orth, Marcel Dekker, 1997).
Friberg, S. E. Micelles, microemulsions, liquid crystals, and the structure of stratum corneum lipids *J. Soc. Cosmet. Chem.*, 1990 (May/Jun.) 41, 155-171, 1990).

* cited by examiner

*Primary Examiner*—Michele Flood
(74) *Attorney, Agent, or Firm*—Forrest L. Collins Law Offices, LLC; Forrest L. Collins

(57) ABSTRACT

The present invention relates generally to the use of botanical extract compositions, which contain ingredients with self-preserving properties for use in cosmetic or dermatological compositions.

4 Claims, No Drawings

BOTANICAL EXTRACT COMPOSITIONS AND PROCESS FOR PREPARING SAME

BACKGROUND OF THE INVENTION

1. Field of the Invention

The present invention relates generally to the use of botanical extract compositions, which contain ingredients with self-preserving properties for use in cosmetic or dermatological compositions. By self-preserving properties, it is meant that the composition incorporating the botanical extract will retard bacterial growth when compared to the composition without the botanical extract. Preservative-free and self-preserving products may be developed by understanding, and applying, the principles of preservation, as they relate to each product. Some of these principles include water activity, pH, the use of special lipids, chelating agents and solvents with known antimicrobial properties.

It is common to introduce into cosmetic or dermatological compositions chemical preservatives intended to retard the growth of microorganisms. Such microorganisms may have the potential to be harmful to consumers if they are likely to grow in the composition or if they are introduced thereto via the fingers repeatedly manipulating the product in a vessel.

Typical conventional cosmetic preservatives include, in particular, parabens and formaldehyde donors, (e.g. DMDM Hydantoin). Although effective against micro-organisms, these preservatives present the drawback of causing intolerance, when used in skin care products, such as irritation, and in particular on sensitive skin. This also is the case for alcohols and certain types of glycols, such as ethanol or propylene glycol, especially when they are used at a relatively high concentration.

Thus, there is a consumer need for cosmetic and dermatological products with self-preserving properties, which are free of conventional preservatives and do not present the drawbacks associated therewith.

2. Description of the Art Practices

U.S. Pat. No. 5,948,416 issued to Wagner, et al. Sep. 7, 1999 discusses skin care compositions comprising: (A) from about 0.001% to about 20% of an active ingredient, (B) from about 1% to about 20% of a stable, hydrophobic, structuring agent selected from the group consisting of saturated $C_{16}$ to $C_{30}$ fatty alcohols, saturated $C_{16}$ to $C_{30}$ fatty alcohols containing from about 1 to about 5 moles of ethylene oxide, saturated $C_{16}$ to $C_{30}$ diols, saturated $C_{16}$ to C30 monoglycerol ethers, saturated $C_{16}$ to $C_{30}$ hydroxy fatty acids, and mixtures thereof, having a melting point of at least about 45 degree. C.; and (C) from about 0.05% to about 10% of a hydrophilic surfactant selected from the group consisting of anionic surfactants, cationic surfactants, zwitterionic surfactants, and mixtures thereof, and (D) from about 25% to about 98.949% water.

U.S. Pat. No. 5,925,364 to Ribier, et al. issued Jul. 20, 1999 relates to a cosmetic or dermatological composition comprising an emulsion of the oil-in-water type formed of oily globules which are each provided with a lamellar liquid crystal coating and are dispersed in an aqueous phase. The Ribier, et al. patent also states each oily globule containing at least one lipophilic compound, which is cosmetically or dermatologically active, is individually coated with a monolamellar or aligolamellar layer obtained from at least one lipophilic surface-active agent, from at least one hydrophilic surface-active agent and from at least one ionic amphiphilic lipid imparting to the emulsion a pH ranging from 5.5 to 7.5, the coated oily globules having a mean diameter of less than 500 nanometers. U.S. Pat. No. 6,066,328 to Ribier, et al. issued May 23, 2000 contains disclosures substantially similar to U.S. Pat. No. 5,925,364 to Ribier, et al.

U.S. Pat. No. 6,211,238 which issued to Castillo, et al. on Apr. 3, 2001 discloses anionic surfactants used in conjunction with an antifungal acid and a chelating agent to preserve topically administrable pharmaceutical compositions without the need for a conventional preservative such as benzalkonium chloride.

U.S. Pat. No. 6,495,498 Niemiec, et al. issued Dec. 17, 2002 discusses "two-in-one" detergent compositions comprised of at least one water soluble silicone agent, at least one cationic conditioning agent, and a detergent. These compositions, according to the Niemiec, et al. patent, are suitable for use in shampoos, baths, and shower gels. Also described in the Niemiec, et al. patent is a delivery system for depositing benefit agents into and onto the skin, nails, and/or hair comprised of at least one water soluble silicone and at least one cationic conditioning agent.

U.S. Pat. No. 4,557,935 af Ekenstam, et al. issued Dec. 10, 1985 recites a germicidal composition which consists of an aqueous suspension of hydrophilic lipid crystals of 1-monolaurin, and preferably also 1-monomyristin, in a quantity of 20–30 percent by weight, and hydrogen peroxide in a quantity of 0.2–5 percent by weight. The hydrophilic lipid crystals stabilize the hydrogen peroxide, to the effect that the composition retains its germicidal power even after having been stored for a long time. According to the af Ekenstam, et al. patent, the peroxide disintegrates slowly when the composition has been applied onto skin or mucous membrane.

U.S. Pat. No. 5,736,574 granted to Burnier, et al., Apr. 7,1998 describes combinatory antimicrobial immixtures comprising at least one antimicrobial hydrolipid and/or lipid and an antimicrobially synergistically effective amount of at least one glyceryl monoalkyl ether are well suited for formulation, as preservatives, into a wide variety of pharmaceutical/cosmetic compositions.

U.S. Pat. No. 5,744,062 Dahms, et al. issued Apr. 28, 1998 recites emulsifier blends that provide a stable oil-in-water emulsion of a preselected viscosity. The emulsifier blend contains an acyl lactylate as the primary emulsifier and a nonionic surfactant as the coemulsifier. A method of preparing an oil-in-water emulsion having a preselected viscosity also is disclosed in the Dahms, et al. patent.

U.S. Pat. No. 6,146,660 Terren, et al. granted Nov. 14, 2000 recites compositions comprising an aqueous dispersion of lipid vesicles having an aqueous core, wherein the dispersion comprises at least one uncoated pigment dispersed in the aqueous phase and wherein the lipid vesicles with an aqueous core and a lipid membrane formed from at least one fatty acid ester, these compositions being stable, of homogeneous color and containing no or virtually no lumps of pigment, and a process for dispersing a filler in an oil-in-water dispersion of lipid vesicles by means of a high-pressure homogenizer.

U.S. Pat. No. 6,274,124 to Vollhardt issued Aug. 14, 2001 recites a method for imparting water resistance to or improving water resistance of a cosmetic or dermatological formulation, comprising adding an water resistance enhancing effective amount of 1,2-pentanediol to the otherwise conventional cosmetic or dermatological formulation comprising at least one cosmetic and/or dermatological active agent in a cosmetically and/or pharmaceutically acceptable carrier for topical application to the skin of humans.

U.S. Pat. No. 6,281,203 issued to Touzan, et al. on Aug. 28, 2001 describes a cosmetic and/or dermatological composition, which contains (i) salicylic acid and/or at least one salicylic acid derivative, (ii) at least one ester of a fatty acid and glucose and/or alkyl glucose, and (iii) at least one oxyethylenated ether of a fatty acid ester of glucose and/or alkylglucose. The composition allows a gentle treatment of the human skin. The composition is useful for treating the effects of skin aging, and treating skin disorders such as acne.

U.S. Pat. No. 6,296,859 Stoltz issued Oct. 2, 2001 describes a composition which comprises as one of the constituents at least one extract and/or of at least one tincture from plants of the Nympheacea family. The composition described in the Stoltz patent is stated to be useful in cosmetics.

U.S. Pat. No. 6,521,241 Minerath, III et al. Feb. 18, 2003 relates to a skin irritant sequestering composition comprising a tissue substrate, a hydrophilic skin irritant sequestering agent and a hydrophobic skin irritant sequestering agent. In one embodiment the sequestering agents are comprised of modified and non-modified clays. In one embodiment the Minerath III et al. patent states, the skin irritants are bound to sequestering agents present on a substrate. In another embodiment the Minerath III et al. patent states the skin irritants are bound to sequestering agents present on the skin.

U.S. Pat. No. 6,524,594 Santora et al. Feb. 25, 2003 recites a gelled oil composition containing an emulsifier, a gelling agent, an oil, and a surfactant which, when applied to the skin in the presence of water, produces a significant amount of foam. The Santora, et al. patent states that after the composition is rinsed from the skin, a non-greasy, oil residue is left thereon.

The reader is also directed to G. Dahms, "Properties of O/W Emulsions with Anisotropic Lamellar Phases," Cosmetics & Toiletries 101:113–115, (1986). The reader is also referred to G. M. Eccleston, "Multiple-Phase Oil-in-Water Emulsions", J. Soc. Cosmet. Chem. 41:1–22 (January/February 1990).

The reader is also directed to Chapter 3 "Water Activity and Self-Preserving Formulas" (Preservative-Free and Self-Preserving Cosmetics and Drugs Principles and Practice, Kabara and Orth, Marcel Dekker, 1997). A reference on liquid crystalline structures which have been reported to interact favorably with stratum corneum lipids, which themselves have been said to be in the form of an amphiphilic association is found in *J. Soc. Cosmet. Chem.*, 41, 155–171, 1990). See also Chapter 3 "Water Activity and Self-Preserving Formulas" (*Preservative-Free and Self-Preserving Cosmetics and Drugs Principles and Practice*, Kabara and Orth, Marcel Dekker, 1997).

To the extent that the foregoing patents and references are relevant to the present invention they are herein incorporated by reference. Temperatures herein are given in degrees Centigrade and pressures are in gauge Kpa. Ratios and ranges may be combined.

SUMMARY OF THE INVENTION

The present invention describes a composition of matter comprising:
A. pentylene glycol;
B. glyceryl laurate;
C. a member selected from the group consisting of capryloyl glycine and undecylenoyl glycine and mixtures thereof; and,
D. water.

Yet another aspect of the invention is a composition of matter comprising an emulsified mixture of water, glyceryl laurate, and pentylene glycol.

Another aspect of the invention is a composition of matter comprising:
A. a first mixture containing pentylene glycol and green tea extract at about 9 parts to 1 part by weight and wherein the weight ratio of the pentylene glycol to the green tea extract is from 9:1 to 1:9;
B. a second mixture containing
a water-soluble salt of ethylenediaminetetracetic acid at about 0.02 to about 2 parts by weight;
a member selected from the group consisting of capryloyl glycine and
undecylenoyl glycine and mixtures thereof at about 0.1 to about 4 parts by weight;
glyceryl laurate at about 0.5 to about 50 parts by weight; and,
water at about 10 to about 90 parts by weight.

Still yet a further aspect of the invention is a composition of matter comprising:
A. a first mixture containing the botanical extract of a mixture of pentylene glycol and a botanical at about 1 part to 10 parts by weight wherein the weight ratio of pentylene glycol to the botanical is about 2:1 to 30:1 and the botanical is selected from the group consisting of grape, green tea, Echinacea, centella Asiatica, Elderflower, Irish moss, and mallow;
B. a second mixture containing a water-soluble salt of ethylenediaminetetracetic acid at about 0.2 to about 2 parts by weight;
a member selected from the group consisting of capryloyl glycine and
undecylenoyl glycine and mixtures thereof at about 0.05 to about 5 parts by weight; glyceryl laurate at about 0.5 to about 50 parts by weight; and,
water at about 10 to about 90 parts by weight, and,
C. glycerin at about 0.5 to about 50 parts by weight.

Yet another aspect of the invention is a composition of matter comprising:
A. a first mixture containing the botanical extract of a mixture of pentylene glycol and a botanical at about 1 part to 10 parts by weight wherein the weight ratio of pentylene glycol to the botanical is about 2:1 to 30:1 and the botanical is selected from the group consisting of grape, green tea, Echinacea, centella Asiatica, Elderflower, Irish moss, and mallow, soap bark, yucca, and Clary Sage;
B. a second mixture containing a water-soluble salt of ethylenediaminetetracetic acid at about 0.2 to about 2 parts by weight;
a member selected undecylenoyl glycine at about 0.05 to about 5 parts by weight;
glyceryl laurate at about 0.5 to about 50 parts by weight; and,
water at about 10 to about 90 parts by weight, and,
C. glycerin at about 0.5 to about 50 parts by weight.

The present invention also describes a composition of matter comprising:
A. a first mixture containing the botanical extract of a mixture of pentylene glycol and a botanical about 1 part to 10 parts by weight wherein the weight ratio of pentylene glycol to the botanical extract is present at about 2:1 to 30:1 and the botanical is selected from the group consisting of grape, green tea, Echinacea, centella Asiatica, Elderflower, Irish moss, and mallow, soap bark, yucca, and Clary Sage;
B. a second mixture containing a water-soluble salt of ethylenediaminetetracetic acid at about 0.2 to about 2 parts by weight;
a member selected undecylenoyl glycine at about 0.1 to about 4 parts by weight;
1-monolaurin at about 5 to about 15 parts by weight; and, water at about 70 to about 90 parts by weight, and,
C. a member selected from the group consisting of a silicone fluid and silicone fluid derivatives and mixtures thereof at about 0.5 to about 5 parts by weight.

Yet another aspect of the present invention is a composition of matter comprising:
A. a first mixture containing pentylene glycol and botanical extract at about 1 part to 10 parts by weight wherein the weight ratio of pentylene glycol to the botanical extract is present at about 2:1 to 30:1 and the botanical extract is selected from the group consisting of grape, green tea, Echinacea, centella Asiatica, Elderflower, Irish moss, and mallow, soap bark, yucca, and Clary Sage;
B. a second mixture containing a water-soluble salt of ethylenediaminetetracetic acid at about 0.2 to about 2 parts by weight;
a member selected undecylenoyl glycine at about 0.1 to about 4 parts by weight;
glyceryl laurate at about 5 to about 15 parts by weight; and, water at about 70 to about 90 parts by weight, and,
C. a member selected form the group consisting of anionic, non-ionic, amphoteric and cationic surfactants and mixtures thereof about 5 to about 25 parts by weight.

DETAILED DESCRIPTION OF THE INVENTION

The present invention relates generally to the use of botanical extract compositions, which contain ingredients with self-preserving properties for use in cosmetic or dermatological compositions. There is a risk of organism resistance taking place that has undesirable consequences. The compositions of the present invention provide "hurdles" to bacterial growth by a variety of different anti-bacterial mechanisms.

In one aspect, the present invention relates to the use of certain aqueous dispersions of hydrophilic lipid crystals of 1-monoglycerides in combination with lipoaminoacids, a chelating agent and pentylene glycol as an extraction vehicle for the creation of a liquid crystalline botanical extract composition with self-preserving properties. In a second aspect of the present invention liquid crystalline botanical extract compositions are incorporated into oil-in-water or water-in-oil emulsions, which may also contain a silicone fluid or a silicone fluid derivative.

The first component of the present invention is pentylene glycol. Pentylene glycol or 1,2-pentanediol is useful as an extraction agent to obtain the botanical extract compositions. The pentylene glycol is also believed to possess antimicrobial properties, which aids in the formation of a self-preserving composition.

The second component of the present invention is the botanical utilized to obtain the botanical extract. The botanicals utilized herein include: *Camellia sinensis* (green tea), grapes, Echinacea, Centella Asiatica, Elderflower, Irish moss, Mallow, soap bark, Yucca, and Clary sage, and mixtures thereof. The botanical utilized to obtain the botanical extract may be obtained from any of the plant parts including the leaves, pulp, seeds, or stems as well as the whole plant.

The third component of the present invention is glyceryl laurate (1-monolaurin). While glyceryl laurate generally refers to a mixture of two isomers the term glyceryl laurate as used in the present invention utilizes that term to refer to the substitution of only one of the terminal hydroxyl hydrogens on a glycerin molecule with lauric acid. The presence of 2-monolaurin in mixture with glyceryl laurate (1-monolaurin) is also useful in the present invention, however, the more pure the glyceryl laurate is (i.e. high 1-monolaurin content) the more effective the product is with respect to self-preserving properties. In practice, it is desired that the amount of 2-monolaurin in mixture with glyceryl laurate (1-monolaurin) is less than 25 percent by weight of the mixture of the 1-monolaurin and the 2-monolaurin. Preferably, the 1-monolaurin content should be at least 90% by weight of the mixture of the 1-monolaurin and the 2-monolaurin.

The fourth component of the present invention is a particular group of lipoamino acid selected from the group consisting of octanoylglycine and undecylenoyl glycine.

The fifth component of the present invention is a water-soluble salt of ethylenediaminetetracetic acid (EDTA). Preferably, the water-soluble salt is the disodium salt of ethylenediaminetetracetic acid. The water-soluble ethylenediaminetetracetic acid salt is effective in improving the efficacy of the other self-preserving ingredients, in the present invention, against Gram-negative bacteria.

In addition to showing antimicrobial properties, the monoglyceride "1-monolaurin" (glyceryl laurate) also exhibits a variety of mesomorphic (between liquid and crystal) states when added to water, followed by heating, mixing and cooling. Such phase transition states are analogous to what is observed with soap and water systems.

At a certain temperature close to the melting point, hydrocarbon chains of the molecules become fluid, and at the same time the water penetrates between the polar groups, resulting in the formation of liquid crystalline structures, which can be of the lamellar, hexagonal, or cubic type.

Hydrophilic lipid crystals of 1-monolaurin are known to have a surface containing hydroxyl groups in an extremely high-density molecular arrangement. Such a molecular configuration favors an ideal surface for creating hydrogen bonds to oxygen atoms (the hydrogen atoms of the surface are hydrogen donors).

Liquid crystalline structures have been reported to interact favorably with stratum corneum lipids, which themselves, have been said to be in the form of an amphiphilic association (Ref. *J. Soc. Cosmet. Chem.*, 41, 155–171, 1990).

The present invention provides a self-preserving botanical extract composition in a hydrophilic liquid crystalline state. When the composition is subsequently added to cosmetic emulsions or aqueous surfactant systems, the delivery of plant-derived extracted "active substances", may be facilitated when applied to skin or hair. In addition, th composition may be used as a carrier for self-preserving antimicrobial agents, which may eliminate the need for conventional preservatives in cosmetic or dermatological formulations.

According to the present invention, topically applied cosmetic and dermatological compositions are self-preserved, without the need for conventional preservative ingredients. Thus, such compositions of the present invention may formulated without any preservatives selected from the group consisting of quaternary ammonium preservatives, such as benzalkonium chloride and benzalkonium bromide; chlorhexidine; cetylpyridinium chloride; parabens, DMDM Hydantoin; and thimerosal.

The present invention also relates to a method of delivering botanical actives to skin using a liquid crystalline film matrix. Among other factors, the present invention is based on the finding that when glyceryl laurate is combined with water and a botanical extract prepared with pentylene glycol, self-preserving aqueous dispersions may be formed, which contain liquid crystalline and/or hydrophilic lipid crystal structures. Such crystalline association compositions may be subsequently added to both "oil-in-water" (O/W) and "water-in-oil" (W/O) emulsion compositions (including "water-in-silicone" (W/S) systems, to create textural and consistency modifications, and enhancements of cosmetic skin-feel attribute aesthetics.

A desirable ingredient, while not required in the compositions of the present invention, is a silicone derivative ingredient such as a dimethicone or cyclomethicone fluid. In particular, one such silicone is product is bis-PEG/PPG-14/14 dimethicone (Abil-97). This ingredient is dimethicone, end-blocked with an average of 14 moles of ethylene oxide and an average of 14 moles of propylene oxide. Another silicone material, which is presently of interest in the present invention, is a "water-in-silicone" emulsion composition containing "Abil EM-90", a non-ionic W/O emulsifier, which is also based on silicone. Abil EM-90 is also known as cetyl PEG/PPG-10/1 dimethicone (a copolymer of cetyl dimethicone containing an average of 10 moles of ethylene oxide and 1 mole of propylene oxide). A further useful silicone in the present invention is dimethylpolysiloxane (e.g. Dow Corning silicone 200 Fluid 350 cs).

The amounts of the recited ingredient may be any useful amount, which aids in making the overall composition self-preserving.

What follows are suggested examples of the present invention.

EXAMPLE 1

Age-Retarding Antioxidant Complex

An age-retarding antioxidant Green Tea Extract #1 is prepared by combining the leaves of *Camellia Sinensis* (Green Tea) and pentylene glycol in a 1:9 ratio, followed by heating at 75° C. and filtration to obtain a clear Green Tea Extract #1 as a liquid:

|  | % w/w |
|---|---|
| A. Green Tea Extract #1 | 5.00 |
| Part B is obtained by mixing and heating the ingredients to 65°–70° C., forming a translucent liquid dispersion: | |
| B. Water | 81.50 |
| Disodium EDTA | 1.00 |
| Capryloyl glycine | 2.50 |
| Glyceryl laurate | 10.00 |
|  | 100.00 |

Part A and Part B are combined at 65° C. with mixing to obtain a self-preserving product. The self-preserving product is then cooled to 55° C. while mixing, forming a thin gel-like translucent liquid crystalline phase. Further slow cooling to 30° C. produces a product with hydrophilic lipid crystals.

EXAMPLE 2

Moisturizing Botanical Complex

A Moisturizing Botanical Extract #2 is prepared by combining the plant parts of a selected botanical blend and pentylene glycol in a 1:1 ratio at 25 C, using a recirculating extraction filtration procedure to obtain a clear Moisturizing Botanical Extract #2 as a liquid:

|  | % w/w |
|---|---|
| A. Moisturizing Botanical Extract #2 | 3.00 |
| Botanical Blend | |
| Whole Grape 30.0% | |
| Green Tea 30.0 | |
| Echinacea 18.5 | |
| Centella Asiatica 18.5 | |
| Elderflower 1.0 | |
| Irish Moss 1.0 | |
| Mallow 1.0 | |
| Part B is obtained by heating the ingredients to 65°–70° C., forming a translucent liquid dispersion: | |
| B. Glycerin | 2.00 |
| Water | 81.50 |
| Disodium EDTA | 1.00 |
| Capryloyl glycine | 2.50 |
| Glyceryl laurate (Lauricidin ® product) | 10.00 |
|  | 100.00 |

Part A and Part B are combined at 65° C. with mixing to obtain a self-preserving product. The self-preserving product is then cooled to 55° C. while mixing, forming a thin gel-like translucent liquid crystalline phase. Further slow cooling to 30° C. produces a product with hydrophilic lipid crystals.

EXAMPLE 3

Cleansing Botanical Complex

A cleansing botanical extract #3 is prepared by combining the plant parts of a selected botanical blend and pentylene glycol in a 1:1 ratio at 25° C., using a recirculating extraction filtration procedure to obtain a clear Cleansing Botanical Extract #3:

|  | % w/w |
|---|---|
| A. Cleansing Botanical Extract #3 | 3.00 |
| Botanical Blend | |
| Whole Grape 30.0% | |
| Green Tea 30.0 | |
| Echinacea 18.5 | |
| Centella Asiatica 18.5 | |
| Soap Bark 1.0 | |
| Yucca 1.0 | |
| Clary Sage 1.0 | |
| Part B is obtained by heating the ingredients to 65°–70° C., forming a translucent liquid dispersion: | |
| B. Glycerin | 2.00 |
| Water | 81.50 |

-continued

| | % w/w |
|---|---|
| Disodium EDTA | 1.00 |
| Undecylenoyl glycine | 2.50 |
| Glyceryl laurate | 10.00 |
| | 100.00 |

Part A and Part B are combined at 65° C. with mixing to obtain a self-preserving product. The self-preserving product is then cooled to 55° C. while mixing, forming a thin gel-like translucent liquid crystalline phase. Further slow cooling to 30° C. produces a product with hydrophilic lipid crystals.

EXAMPLE 4

Age-Retarding Hydrophilic Lipid Crystal Green Tea Lotion

An age-retarding hydrophilic lipid crystal lotion is prepared by combining the ingredients of Parts A and B at 75° C., followed by cooling to 45° C. and the addition of Part C to the mixture of Part A and Part B produces a self-preserving age-retarding lipid crystal cosmetic product.

| | | % w/w |
|---|---|---|
| A. | Water | 79.05 |
| | Xanthan gum | 0.20 |
| B. | C12–15 alkyl benzoate | 3.00 |
| | Stearic acid | 3.50 |
| | Glyceryl stearate | 1.00 |
| | Caprylic/Capric triglyceride | 1.00 |
| | Cetyl Alcohol | 0.75 |
| | Sorbitan 60 | 0.25 |
| | Polysorbate 80 | 0.25 |
| | Dimethicone | 1.00 |
| C. | Age-Retarding Antioxidant Complex (per EXAMPLE 1) | 10.00 |
| | | 100.00 |

EXAMPLE 5

Moisturizing Hydrophilic Lipid Crystal Emulsion

A moisturizing hydrophilic lipid crystal emulsion is prepared by heating Part A and Part B to 75° C., followed by the addition of Part B to A. After cooling to 30° C., the addition of Part C to the mixture of Part A and Part B yields a self-preserving hydrophilic lipid crystal emulsion.

| | | % w/w |
|---|---|---|
| A. | Polyglyceryl-4 Isostearate | 2.50 |
| | Cetyl PEG/PPG-10/1 Dimethicone | 1.50 |
| | Ethylhexyl palmitate | 9.00 |
| | Cyclopentasiloxane | 5.00 |
| | Hexyl Laurate | 1.00 |
| | White Beeswax | 1.25 |
| B. | Water | to 100 |
| C. | Moisturizing Botanical Complex (per EXAMPLE 2) | 10.00 |
| | | 100.00 |

EXAMPLE 6

Hydrophilic Lipid Crystal Daily Cleanser

A hydrophilic lipid crystal daily cleanser is prepared by heating parts A and B to 75° C. followed by the addition of Part B to Part A. After cooling to 30° C., the addition of part C yields a self-preserving skin cleansing product.

| | | % w/w |
|---|---|---|
| A. | Water | 69.30 |
| | Carbomer | 0.70 |
| B. | PEG-7 Glyceryl cocoate | 12.00 |
| | Sucrose cocoate | 0.50 |
| | Decyl glucoside | 7.50 |
| C. | Cleansing Botanical Complex (per EXAMPLE 3) | 10.00 |

EXAMPLE 7

Treatment Botanical Complex

A treatment botanical complex is prepared by combining the plant parts of a selected botanical blend and pentylene glycol in a 1:1 ratio at 25° C., using a recirculating extraction procedure to obtain a clear Treatment Botanical Extract #7:

| | | | | |
|---|---|---|---|---|
| A. | Treatment Botanical Extract #7 | | | 0.50 |
| | Botanical Blend | | | |
| | Whole Grape | 30.00 | | |
| | Green Tea | 30.00 | | |
| | Echinacea | 18.50 | | |
| | Centella Asiatica | 18.50 | | |
| | Licorice | 1.00 | | |
| | Olive Leaf | 1.00 | | |
| | Red Clover | 1.00 | | |
| | Part B is obtained by heating the ingredients to 65°–70° C., forming a translucent liquid dispersion: | | | |
| B. | Glycerin | | | 2.00 |
| | Water | | | 84.00 |
| | Disodium EDTA | | | 1.00 |
| | Capryloyl glycine | | | 2.50 |
| | Glyceryl laurate | | | 10.00 |
| | | | | 100.00 |

Part A and Part B are combined at 65° C. with mixing to obtain a self-preserving product. The mixture of Part A and Part B is then cooled to 55° C. while mixing, to form a thin gel-like translucent liquid crystalline phase. Further cooling to 30° C. produces hydrophilic lipid crystals.

EXAMPLE 8

Lipid Crystal Hair Treatment

A hydrophilic lipid crystal hair treatment composition is prepared by heating Parts A and B separately to 75° C., followed by the addition of part B to part A. After cooling to Parts A and B to 30° C., the addition of part C yields a self-preserving hydrophilic lipid crystal hair treatment.

|   |   | % w/w |
|---|---|---|
| A. | Water | 75.75 |
|   | Panthenol | 0.75 |
| B. | Behentrimonium chloride | 1.25 |
|   | Cetearyl alcohol | 3.75 |
|   | Cetrimonium chloride (30%) | 3.50 |
|   | Cetearyl ethylhexanoate | 2.00 |
|   | Polyisobutylene | 1.50 |
|   | Myristyl alcohol | 1.50 |
| C. | Treatment Botanical Complex (per EXAMPLE 7) | 10.00 |
|   |   | 100.00 |

What is claimed is:

1. A composition of matter comprising:
   A. a first mixture containing pentylene glycol and a botanical extract at about 1 part to 10 parts by weight wherein the pentylene glycol to the botanical extract is at about 2:1 to 30:1 parts by weight and the botanical extract is, green tea (*Camellia Sinensis* Leaf Extract);
   B. a second mixture containing a water-soluble salt of ethylenediaminetetracetic acid at about 0.2 to about 2 parts by weight; undecylenoyl glycine at about 0.1 to about 4 parts by weight; glyceryl laurate at about 5 to about 15 parts by weight; and, water at about 70 to about 90 parts by weight; and,
   C. a member selected from the group consisting of anionic, non-ionic, amphoteric and cationic surfactants and mixtures thereof at about 5 to about 25 parts by weight.

2. The composition of matter of claim 1 wherein the glyceryl laurate is a mixture of 1-monolaurin and 2-monolaurin and wherein the 1-monolaurin comprises at least 75% of the mixture.

3. A composition of matter comprising:
   A. a first mixture containing pentylene glycol and a botanical extract at about 1 part to 10 parts by weight wherein the weight ratio of pentylene glycol to the botanical extract is at about 2:1 to 30:1 and the botanical extract is green tea (*Camellia Sinensis* Leaf Extract);
   B. a second mixture containing a water-soluble salt of ethylenediaminetetracetic acid at about 0.2 to about 2 parts by weight; undecylenoyl glycine at about 0.1 to about 4 parts by weight; glyceryl laurate at about 5 to about 15 parts by weight; and, water at about 70 to about 90 parts by weight;
   C. a member selected from the group consisting of anionic surfactants at about 5 to about 25 parts by weight; and
   D. provided further that the glyceryl laurate in the second mixture is in the form of a liquid crystal.

4. The composition of matter of claim 3 wherein the glyceryl laurate is a mixture of 1-monolaurin and 2-monolaurin and wherein the 1-monolaurin comprises at least 75% of the mixture.

* * * * *